United States Patent
Slaugh et al.

(10) Patent No.: US 6,175,050 B1
(45) Date of Patent: Jan. 16, 2001

(54) PROCESS FOR SEPARATING FUNCTIONALIZED ALPHA OLEFINS FROM FUNCTIONALIZED INTERNAL OLEFINS

(75) Inventors: Lynn Henry Slaugh; Laurent Alain Fenouil, both of Houston; Howard Lam-Ho Fong, Sugar Land, all of TX (US)

(73) Assignee: Shell Oil Company, Houston, TX (US)

( * ) Notice: Under 35 U.S.C. 154(b), the term of this patent shall be extended for 0 days.

(21) Appl. No.: 09/310,054

(22) Filed: May 11, 1999

(51) Int. Cl.$^7$ .................. C07C 7/00; C07C 7/10
(52) U.S. Cl. .............. 585/867; 585/809; 585/833; 585/866
(58) Field of Search ................ 585/809, 833, 585/866, 867

(56) References Cited

U.S. PATENT DOCUMENTS

| | | | |
|---|---|---|---|
| 4,915,794 | 4/1990 | Slaugh et al. ............. | 203/29 |
| 4,946,560 | 8/1990 | Slaugh et al. ............. | 203/38 |
| 5,012,034 | 4/1991 | Weingaertner et al. ...... | 585/806 |
| 5,936,136 * | 8/1999 | Slaugh et al. ............. | 585/867 |
| 5,942,656 * | 8/1999 | Slaugh et al. ............. | 585/864 |
| 6,018,089 * | 1/2000 | Slaugh et al. ............. | 585/867 |

OTHER PUBLICATIONS

U.S. application Ser. No. 08/987,553, Slaugh et al., filed Dec. 9, 1997.
U.S. application Ser. No. 08/876,822, Slaugh et al., filed Jun. 16, 1997.
U.S. application Ser. No. 08/987,555, Slaugh et al., filed Dec. 9, 1997.
U.S. application Ser. No. 08/987,554, Weinmann et al., filed Dec. 9, 1997.
U.S. application Ser. No. 08/987,554, Slaugh et al., filed Dec. 9, 1997.
U.S. application Ser. No. 09/309,417, Slaugh et al., filed May 11, 1999.

* cited by examiner

*Primary Examiner*—Benjamin L. Utech
*Assistant Examiner*—Tam M. Nguyen
(74) *Attorney, Agent, or Firm*—Dennis V. Carmen

(57) ABSTRACT

This invention relates to a process for separating functionalized alpha olefins from functionalized internal olefins. The process achieves by a step of contacting a feedstock containing functionalized alpha olefins and functionalized internal olefins with a linear polyaromatic compound to form a linear polyaromatic compound-functionalized alpha olefin adduct and a step of dissociating the linear polyaromatic compound-functionalized alpha olefin adduct to form linear polyaromatic compounds and a functionalized alpha olefin composition.

25 Claims, No Drawings ns from functionalized internal olefins.

1. FIELD OF THE INVENTION

This invention relates to a process for separating functionalized alpha olefins from functionalized internal olefins.

2. BACKGROUND OF THE INVENTION

Many industrial processes produce olefins that are mixtures of functionalized internal olefins and functionalized alpha olefins. Olefins are frequently used in the manufacture of polymers, as drilling mud additives or as intermediates for the production of oil additives and detergents. Functionalized olefins, and in particular functionalized alpha olefins, may be used in applications such as polymers and chemical intermediates.

Depending upon the particular application, it would be desirable to manufacture a functionalized alpha olefin composition having the greatest purity possible. While pure species of functionalized alpha and internal olefins with a narrow carbon number range can be manufactured or produced in small quantities at a great cost, we have found that it would be particularly desirable to economically provide large quantities of separated and purified functionalized alpha and functionalized internal olefins from commercial raw feedstocks containing a mixture of functionalized internal olefins and functionalized alpha olefins. Examples include feeds containing the synthetic reaction products of syn-gas, such as those found in Fisher-Tropsch streams; by the oxidation of unsaturated and saturated hydrocarbons which often form unsaturated by-products; and the dehydrogenation of oxygenated hydrocarbons.

Separating and isolating functionalized alpha olefins from functionalized internal olefins is no easy task, especially when these species have similar or identical molecular weights or carbon numbers or when the only difference in the species one desires to separate is the position of the double bond. Conventional distillation methods are frequently inadequate to separate species of this type, which have such closely related boiling points. The separation problem is further aggravated in that the functionalized alpha olefin species not only needs to be separated from functionalized internal olefins, but also from those species containing differing functional groups and the saturated hydrocarbons.

U.S. Pat. No. 4,946,560 described a process for the separation of internal olefins from alpha olefins by contacting a feedstock with anthracene to form an olefin adduct, separating the adduct from the feedstock, dissociating the olefin adduct through heat to produce anthracene and an olefin composition enriched in alpha olefin, and separating out the anthracene from the alpha olefin. This reference does not suggest the desirability or the capability of anthracene to conduct a separation operation between functionalized alpha olefins and functionalized internal olefins.

3. SUMMARY OF THE INVENTION

This invention relates to a process for separating functionalized alpha olefins from functionalized internal olefins. In particular, there is provided a process for treating a feedstock comprised of functionalized alpha olefins and functionalized internal olefins, comprising:

a) contacting the feedstock with a linear polyaromatic compound under conditions effective to form a reaction mixture comprising a linear polyaromatic compound-functionalized alpha olefin adduct;

b) separating the linear polyaromatic compound-functionalized alpha olefin adduct, and optionally the unreacted linear polyaromatic compound as well, from the reaction mixture, to form a functionalized adducted alpha olefin stream and a functionalized internal olefin stream;

c) dissociating the linear polyaromatic compound-functionalized alpha olefin adduct in said functionalized adducted alpha olefin stream to form a linear polyaromatic compound and a functionalized alpha olefin composition, and optionally d) separating the linear polyaromatic compound formed in step c) from a functionalized alpha olefin composition; whereby the concentration of functionalized alpha olefin in said alpha olefin composition is enriched in functionalized alpha olefin over the concentration of functionalized alpha olefin in the feedstock. In another embodiment of the invention, the concentration of functionalized internal olefin in the internal olefin stream is enriched in functionalized internal olefin over the concentration of functionalized internal olefin present in the feedstock.

4. DETAILED DESCRIPTION OF THE INVENTION

As used throughout this specification and in the claims, the term "comprising" means "at least," such that other unmentioned elements, ingredients, or species are not excluded from the scope of invention.

Functionalized olefins, whether internal or alpha, are lo compounds with at least one double bond located on an aliphatic or cycloaliphatic moiety of the compound, and the olefin has a functional group, other than C—C unsaturation. Examples of chemically reactive functional groups are carboxyl, aldehyde, keto, thio, ester, ether, hydroxyl, and amine. The number of functional groups on a molecule is not limited. The functional groups may be located anywhere along the carbon backbone.

The functionalized olefins may contain aryl moieties along with an aliphatic or cycloaliphatic moiety within the same compound, or may consist solely of an aliphatic, cycloaliphatic, or cycloaliphatic with aliphatic moieties on the compound. Preferably, the functionalized olefin is an aliphatic compound.

The functionalized olefin may be branched or linear. Examples of branching include alkyl, aryl, or alicyclic branches. The number of unsaturation points along the chain is also not limited. The olefin may be a mono-, di-, tri-, etc unsaturated olefin, optionally conjugated.

A functionalized alpha olefin is an olefin whose double bond is located on both of any $\alpha$ and its $\beta$ carbon atoms. An $\alpha$ carbon atom is any terminal carbon atom, regardless of how long the chain is relative to other chain lengths in a molecule. The location of any branches or additional functional groups on the functionalized alpha olefin is not limited. Branches or functional groups compatible with double bonds may be located on double bond carbon atoms, on carbon atoms adjacent to the double bond carbon atoms, or anywhere else along the carbon backbone. The functionalized alpha olefin may also be a poly-ene, wherein two or more points of unsaturation may be located anywhere along the molecule, so long as at least one double bond is in the alpha position.

A functionalized internal olefin(s) is an olefin whose double bond is located anywhere along the carbon chain except at any terminal carbon atom. The location of a branch or a functional group on the functionalized internal olefin is not limited. Branches or functional groups may be located on the double bond carbon atoms, on carbon atoms adjacent to the double bond carbon atoms, or anywhere else along the carbon backbone.

Examples of functionalized olefins include unsaturated fatty acids, $\alpha,\beta$-unsaturated acids and esters, $\omega$-unsaturated acids and esters, $C_5$–$C_{20}$ alpha or internal primary alcohols, and $C_5$–$C_{20}$ alpha or internal ketones and aldehydes.

The feedstock olefins used in the process of the invention comprise functionalized alpha olefins and functionalized internal olefins. The feedstock may optionally contain other kinds of olefins, such as linear and/or branched internal and alpha olefins, as well as aromatic compounds and paraffins. The feedstock is generally produced by commercial processes such as the oxidation of saturated and unsaturated hydrocarbons or the dehydrogenation of functionalized hydrocarbons. Alternatively, the feedstock may be produced by the Fisher-Tropsch process, which often contains functionalized species. A Fisher-Tropsch process catalytically hydrogenates CO and advances toward the production of compositions containing aliphatic molecular chains. The most preferred feedstock is that obtained from a Fisher-Tropsch (FT) synthesis.

FT catalysts and reaction conditions can be selected to provide a particular mix of species in the reaction product stream. For example, the particular catalyst and reaction conditions may be tuned to enhance the amount of olefins and decrease the amount of paraffins and oxygenates in the stream. Alternatively, the catalyst and reaction conditions may be tuned to enhance the amount of paraffins and decrease the amount of olefins and oxygenates in the stream.

FT catalysts and reaction conditions can be selected to provide a particular mix of species in the reaction product stream. For example, the particular catalyst and reaction conditions may be tuned to enhance the amount of olefins and decrease the amount of paraffins and oxygenates in the stream. Alternatively, the catalyst and reaction conditions may be tuned to enhance the amount of paraffins and decrease the amount of olefins and oxygenates in the stream.

Generally, the reaction conditions will vary depending on the type of equipment employed. The FT reaction temperatures vary between 100° C. to 500° C., an inlet gas pressure to the reactor from atmospheric to 1500 psig, and an $H_2$/CO ratio from 0.5:1 to 5:1, preferably from 1.8:1 to 2.2:1, and gas hourly space velocity ranging from 1 to 10,000 v/v/hour. A variety of reactor vessel configurations can be used, including a fluidized (entrained) bed, a fixed bed, and a slurried bed. The temperature in these beds can be adjusted by those of ordinary skill to optimize the formation of FT products, including hydrocarbons, and particularly, olefins and types of olefins. To illustrate without limitation, in fluidized (entrained) bed(s), the temperature of reaction is generally high- e.g. ranging from 280° to 350° C., preferably 310° to 340° C. If a fixed bed reactor(s) is used, the reaction temperature is generally ranges within 200° C. to 250° C., preferably between 210° and 240° C., and when a slurry bed reactor(s) is used, the temperature is generally within the range of 190° C. to 270° C.

The catalyst used in the FT process is any known in the art, but preferably from among Mo, W, and Group VIII compounds, including iron, cobalt, ruthenium, rhodium, platinum, palladium, iridium, osmium, combinations of the foregoing, combinations with other metals, and each being in the free metal form or as alloys, or as an oxide or carbide or other compound, or as a salt. Iron based and cobalt based catalysts have found common commercial use, and ruthenium has gained importance as a metal for the catalyst which favors the formation of high melting waxy species under high pressure conditions. Those of skill in the art recognize which catalysts and combinations will favor the manufacture of desired species in the FT reaction composition. For example, fused iron containing a promoter such as potassium or oxides on a silica, alumina, or silica-alumina support are known as FT synthetic catalysts. Another example is the use of Co metal. Cobalt has the advantage of producing less methane during synthesis over the older nickel based catalysts, and produces a wide spectrum of species. With the proper selection of supports, promoters, and other metal combinations, the cobalt catalyst can be tuned to manufacture a composition rich in the desired species. Other catalysts, such as iron-cobalt alloy catalysts, are known for their selectivity toward olefins under certain process conditions.

The catalysts may be fused or precipitated, or sintered, cemented, impregnated, kneading or melting onto a suitable support.

The catalysts may also contain promoters to promote the catalyst's activity, stability, or selectivity. Suitable promoters include alkali or alkaline earth metals, in free or combined form as an oxide, hydroxide, salt, or combinations thereof.

An FT stream generally contains virtually no sulfur or nitrogen compounds, which may be deleterious to other catalysts which derivatize the olefins or catalyze the reaction of olefins in other oligomerization or polymerization processes. Regardless of the method used, however, the FT process is not very selective to a particular species, and yields a wide variety of species within a composition.

Examples of some of the species found in any FT stream include paraffins having a broad spectrum of molecular weights, alcohols, acids, ketones, and aldehydes, and small amounts of aromatics. The linear polyaromatic compound used in the process of the invention, however, is particularly well adapted for separation of alpha and internal olefin and functionalized olefin species in a FT stream since the presence of oxygenates and other functional groups do not significantly impair the performance of the linear polyaromatic compound.

While reference is made to a FT stream, it is to be understood that any stream made by any process containing olefins and saturated hydrocarbons are suitable feedstocks for the process of the invention. Most crude FT streams contain from 5% to 99% olefins, the remainder being saturated hydrocarbons comprising paraffins and cycloparaffins, and optionally other compounds such as aromatics optionally containing saturated or unsaturated alkyl branches, and oxygenates, based on the weight of all ingredients in the feedstock stream to the process of the invention. The preferred amount of olefin present in the FT stream ranges from 15 wt. % to 70 wt. %. The amount of linear alpha olefin in the FT stream is not limited, but preferably ranges from 15 wt. % to 60 wt. %. The amount of other olefins, including branched olefins and internal olefins, both linear and branched, is also not limited, but preferably ranges from 1 wt. % to 55 wt. %, more typically from 5 wt. % to 45 wt. %.

The amount of functionalized alpha olefins, functionalized internal olefins, and other optional ingredients present in the feedstock is not particularly limited. In fact, the feedstock may contain as little as 3 wt. % of functionalized alpha olefins and up to 95% of functionalized internal olefins, based on the weight of all ingredients in the feedstock. However, the process of the invention is particularly suited to an industrial scale production of functionalized alpha and functionalized internal olefin streams.

Accordingly, in a preferred embodiment of the invention, the feedstock to be treated according to the process of the invention contains at least 5 wt. % of functionalized olefins, more preferably at least 8 wt. % of functionalized olefins, based on the weight of all ingredients in the feedstock. In a preferred embodiment, the feedstock contains up to 50 wt. % of functionalized olefins, more preferably up to 30 wt. % functionalized olefins, and most streams available commercially will have less than 20 wt. % functionalized olefins, based on the weight of all ingredients in the FT stream and feedstock.

It is desirable to employ a feedstock containing at least 3 wt. %, and up to 45 wt. %, more preferably up to 25 wt. %, and most preferably less than 18 wt. % of functionalized alpha olefin, based on the weight of all ingredients in the feedstock. The amount of functionalized alpha olefin, based on the weight of functionalized olefins in the feedstock, is not limited but is generally at least 20 wt. % to justify a separation process and yield desired product. It is generally more desirable to separate functionalized alpha olefins from functionalized internal olefins when the amount of functionalized alpha olefin ranges from 25 wt. % to 90 wt. %, and the amount of functionalized internal olefins ranges from 10 wt. % to 75 wt. %, each based on the weight of functionalized olefins in the feedstock.

The feedstock may be a processed FT stream which has been fractionated and/or purified by a conventional distillation, extraction, or other separation operation to remove some of the paraffins, high and low molecular weight species, and oxygenates from the crude stream. When the separation operation is conducted by distilling the reaction mixture containing the adduct, it is preferred that the feedstock used in the process of the invention contain an average carbon number ranging from $C_5$–$C_{20}$ and wherein the predominant olefin species in the feedstock is within the range of $C_5$–$C_{20}$, inclusive. The polyaromatic adducting compound efficiently separates the saturated hydrocarbons from the olefins when the average carbon number of the feedstock and the predominant olefinic species is within this range, inclusive. When the average carbon number of the feedstock exceeds $C_{20}$, the polyaromatic compound-olefin adduct boils at a lower temperature than many of the species in the $C_{20}$+feedstock composition, thereby leaving these high boiling species in the reaction mixture bottoms containing the adduct. Accordingly, the particular polyaromatic compound and the particular feedstock composition should be so selected that the polyaromatic compound-olefin adduct composition in the reaction mixture boils at a higher temperature than the amount of unreacted paraffin species in the feedstock one desires to separate. Therefore, in this preferred embodiment, the feedstock stream is one which contains an average carbon number ranging from $C_5$–$C_{20}$, and more preferably ranging from $C_6$–$C_{16}$, and wherein the predominant olefin species is within these ranges, inclusive. These types of FT streams are generally processed by one of the techniques identified above to substantially remove cuts containing ingredients below or exceeding the range of $C_5$–$C_{20}$.

In the event that one desires to employ a feedstock outside of the range of $C_5$–$C_{20}$, other separation techniques can be used to separate the adduct from the unreacted reaction mixture, including the selection of higher boiling polyaromatic compounds and/or other separation techniques such as liquid/liquid extraction or crystallization. These techniques, of course, can also be used with feedstocks within the range of $C_5$–$C_{20}$, inclusive.

The linear polyaromatic compound is utilized in the instant process to form the adduct with the functionalized alpha olefins in the feed stream. While not being bound to a theory, it is believed that the linear polyaromatic compound preferentially forms an adduct with the functionalized alpha olefins and to a lesser extent with the functionalized internal olefins. The preferential adduction of linear polyaromatic compound toward the functionalized alpha olefin over the functionalized internal olefins may be due to the steric hindrance and/or electronic effects of the latter olefins in a Diels-Alder reaction.

As used herein, "linear polyaromatic compound" refers to a linear polyaromatic compound having at least three fused aromatic rings, which may be unsubstituted or substituted and possess similar adducting properties as the unsubstituted molecule, and mixtures thereof. The linearity should extend to at all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a hydrocarbon chain, an ether linkage, or a ketone group containing chain so long as at least three fused rings are present in a linear arrangement; as well as those containing a heteroatom which do not interfere in the separation of the functionalized alpha olefins from the functionalized internal olefins.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected so that they are relatively inert under the reaction conditions and relatively small to avoid sterically hindering the formation of the Diels-Alder adduct. Suitable substituted linear polyaromatic compounds can be determined by routine experimentation. Examples of suitable linear polyaromatic compounds include 9,10-dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene.

The process of the instant invention is basically a three step process wherein (a) a linear polyaromatic compound is reacted with a feedstock containing at least functionalized alpha olefins and functionalized internal olefins to at least form an adduct of a functionalized alpha olefin-linear polyaromatic compound, (b) the adduct and the unreacted reaction mixture are separated from each other to form a functionalized internal olefin stream and an adducted functionalized alpha olefin stream, and (c) the adduct is dissociated to release the functionalized alpha olefin and regenerate the linear polyaromatic compound. The Diels-Alder adduct forming reaction is carried out in a conventional fashion and reaction zone. An example of a suitable reaction zone is a continuously stirred tank reactor wherein olefin and linear polyaromatic compound are added continuously to a stirred tank, and the reaction mixture is continuously withdrawn from the stirred tank. Alternatively, the reaction may be carried out in a batch reactor, wherein the olefin and the linear polyaromatic compound are charged to an autoclave, which is then heated to a reaction temperature sufficient to complete the reaction.

The adducting reaction is typically carried out over a range of temperatures from about 150° to about 290° C., preferably from about 200° to about 280° C., and most preferably from about 240° to about 265° C. Pressures are not critical and typically run from about atmospheric to about 100 atmospheres. The reaction can be carried out in the gas phase under vacuum or liquid phase or mixed gas-liquid phase, depending on the volatility of the feedstock, but generally in the liquid phase.

Stoichiometric ratios or an excess of either olefin or linear polyaromatic compound can be used to form the adducts. The molar ratio of olefin to linear polyaromatic compound is preferably from 0.25:1 up to 10:1. The residence time is for a time sufficient to adduct the desired amount of linear polyaromatic compound with the olefin. Typical residence times range from 30 minutes to 4 hours in a batch reaction.

An inert solvent can be utilized to dissolve the feedstock olefins or the linear polyaromatic compound or both in the reactor. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

In one embodiment of the invention, however, the feedstock adduction, and particularly, the linear polyaromatic compound-functionalized alpha olefin adduct formation is carried out in the absence of a solvent to improve the rate or reaction and avoid additional equipment and process steps for separating the solvent.

After the linear polyaromatic compound-functionalized alpha olefin adduct has been formed, it is separated from the reaction mixture to form a functionalized alpha olefin composition and a linear polyaromatic compound composition. The olefin-linear polyaromatic compound adduct may be separated from the reaction mixture by conventional means. Due to the large molecular weight and structural difference between the linear polyaromatic compound-functionalized alpha olefin adduct and the remainder of the reaction mixture, conventional separation techniques are quite suitable for removing the unreacted olefins, and in particular, the unreacted functionalized internal olefins from the linear polyaromatic compound-functionalized alpha olefin adduct, to form a functionalized internal olefin stream. For example, the unreacted olefins may be removed at the overhead or in fractions by vacuum or flash distillation of the reaction mixture to leave the linear polyaromatic compound-functionalized alpha olefin adduct and unreacted linear polyaromatic compound as a liquid slurry bottoms. A substantial amount of other unreacted components of the reaction mixture, if present, such as paraffins, aromatics, and unreacted alcohols, ketones, acids, and other impurities, may be distilled off. Alternatively, the linear polyaromatic compound-functionalized alpha olefin adduct is separated by cooling the reaction mixture until the adduct crystallizes out, followed by filtration or centrifugation to remove the unreacted olefin.

In most cases any unreacted linear polyaromatic compound will separate out with the linear polyaromatic compound-functionalized alpha olefin adduct. The remainder of the separated reaction mixture comprised of functionalized internal olefins can be used in other processes or applications since it has an enriched functionalized internal olefin concentration over that of the feedstock.

The next step of the instant process is to dissociate the linear polyaromatic compound-functionalized alpha olefin adduct. The dissociation process can be accomplished by heating or pyrolyzing the recovered linear polyaromatic compound-functionalized alpha olefin adduct at a temperature ranging from about 250° to about 400° C., preferably from about 300° to about 350° C. This pyrolysis frees the functionalized alpha olefins from the linear polyaromatic compound to form a functionalized alpha olefin composition. The residence time of the adducts in the dissociation zone is short, from 10 seconds to 30 minutes, under subatmospheric to mild pressure generally not exceeding 10 atmospheres.

The linear polyaromatic compound is optionally, but preferably, separated from the resulting mixture by any conventional means. The separation may occur simultaneously with the pyrolysis operation, such as by vacuum or flash distilling off the functionalized alpha olefins along with any impurities at the pyrolysis temperatures, and removing the linear polyaromatic compound as a bottoms from the adduct dissociating zone. Other separation techniques include filtration and centrifugation. The linear polyaromatic compound may be recycled back to the adduct reaction zone.

The concentration of functionalized alpha olefin composition is enriched in functionalized alpha olefin content over that of the feedstock, and the concentration of the functionalized internal olefins in the functionalized alpha olefin composition is reduced over that of the feedstock. In another embodiment, the concentration of functionalized internal olefin in the functionalized internal olefin stream is enriched by the process of the invention over the concentration of functionalized internal olefins present in the feedstock, and the concentration of functionalized alpha olefins in the functionalized internal olefin stream is reduced over the concentration of functionalized alpha olefins present in the feedstock. For purposes of calculation, the concentration of olefins in the feedstock and in the product streams are exclusive of solvent which may be added to an adducting zone or solvents added to the product streams.

While most of the functionalized alpha olefins will have been separated from the functionalized internal olefins, a small amount of functionalized internal olefins, along with other impurities may be present in the final functionalized alpha olefin composition. For many applications, the amount of functionalized internal olefins in the functionalized alpha olefin composition after one cycle through the process of the invention is sufficiently small that only one pass through the process is necessary. If desired, however, the functionalized alpha olefin composition may be subjected to multiple passes through additional adducting and dissociation zones fed by the functionalized alpha olefin composition produced from the prior pass, to further reduce the functionalized internal olefin content and further enhance the functionalized alpha olefin content. In one embodiment, the process of the invention is repeated more than once, more preferably 2–4 times.

In one embodiment, the concentration of functionalized alpha olefin in the functionalized alpha olefin composition is enriched in one pass by at least 30%, preferably by at least 40%, more preferably by at least 60%, relative to the concentration of functionalized alpha olefin present in the feedstock.

In another embodiment, the concentration of functionalized internal olefin in the functionalized alpha olefin composition can be reduced through the process of the invention in only one pass by at least 20%, preferably by at least 30%, more preferably by at least 40%, and as much as at least 60%.

In yet another embodiment, the concentration of functionalized internal olefins in the functionalized alpha olefin composition is less than 3 wt. % after subjecting the feedstock to the process of the invention, based on the weight of all ingredients in the functionalized alpha olefin composition. Preferably, the amount of functionalized internal olefins in the functionalized alpha olefin composition is 2.5 wt. % or less, more preferably 2.0 wt. % or less, most preferably 1.5 wt. % or less. With multiple passes, the content of the functionalized internal olefins can be reduced in the functionalized alpha olefin composition to 1.0 wt. % or less, more preferably 0.7 wt. % or less, most preferably 0.5 wt. % or less.

do not contemplate that these sample feedstocks will be the types of feedstocks used commercially, but using a feedstock of 100% functionalized olefins illustrates in a focused manner the capability of the linear polyaromatic adducting compound to separate internal and alpha functionalized olefins.

0.054 moles of anthracene was charged to a 100 ml. Parr autoclave, purged three times with nitrogen, and sealed. The autoclave was placed in a dry box and 0.108 moles of a nitrogen purged functionalized olefin feedstock sample was added to the autoclave, along with 10 ml. of dry, nitrogen-purged toluene. The autoclave was sealed, removed from the dry box, purged three times with nitrogen, placed in a heating mantle and heated to 255° C. The reaction proceeded for about 1 hour. The autoclave contents were stirred during heating. Once the reaction was complete, the autoclave was cooled to 20° C. The unreacted, excess olefin feedstock was removed by distillation from the product mixture. The remaining bottoms of unconverted anthracene and the anthracene-functionalized alpha olefin adduct mixture was then heated to 300–350° C. for about 0.5 hours, during which time the anthracene-functionalized alpha olefin adduct dissociated to recyclable anthracene and the functionalized alpha olefin composition product enriched in functionalized alpha olefins relative to the concentration of functionalized alpha olefins in the feedstock.

This functionalized alpha olefin composition was analyzed by gas chromatography. The results are shown in Table 1. The concentration of the species within the feedstock and within the resulting functionalized alpha olefin composition is reported as mole percentages.

TABLE 1

SEPARATION OF ALPHA AND INTERNAL FUNCTIONALIZED OLEFINS

| SAMPLE | COMPOSITION | 4-HEXEN-3-ONE | 5-HEXEN-2-ONE | 4-HEXEN-1-OL | 5-HEXEN-1-OL | 3-HEXEN-1-OL | 5-HEXEN-2-OL |
|---|---|---|---|---|---|---|---|
| 1 | Feedstock | 59.9 | 40.1 | — | — | — | — |
| 1 | Product | 33.2 | 66.8 | — | — | — | — |
| 2 | Feedstock | — | — | 50.9 | 49.1 | — | — |
| 2 | Product | — | — | 30.4 | 69.6 | — | — |
| 3 | Feedstock | — | — | — | 50.1 | 49.1 | — |
| 3 | Product | — | — | — | 80.0 | 20.0 | — |
| 4 | Feedstock | 33.5 | — | 33.5 | 33.0 | — | — |
| 4 | Product | 25.7 | — | 18.1 | 56.2 | — | — |
| 5 | Feedstock | — | 50.0 | — | — | — | 50.0 |
| 5 | Product | — | 51.1 | — | — | — | 48.9 |

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention. The present invention will now be illustrated by means of the following illustrative embodiments and examples which are provided for illustration and are not to be construed as limiting the invention.

EXAMPLE

To illustrate the concept of the invention, several samples of six-carbon atom functionalized olefins having different compositions were used as the feedstocks. The composition of each feedstock sample is set forth in Table 1 below. We The results indicate that in each sample, the amount of functionalized alpha olefin was enriched in the product stream. The concentration of functionalized alpha olefin was enriched by 66% in the Sample 1 product stream, by 42% in Sample 2, by 60% in Sample 3, and by 70% in Sample 4. Further, the concentration of functionalized internal olefin in the functionalized alpha olefin stream was reduced, relative to the feedstock. In some cases, the amount of functionalized internal olefin was reduced by more 40%, and even by 60%, over the amount present in the feedstock.

As can be seen in comparison example 5, anthracene is not selective towards the type of functionalization, but rather is selective to the position of the double bond.

What we claim is:

1. A process for treating a feedstock comprised of functionalized alpha olefins and functionalized internal olefins, comprising:

a) contacting the feedstock with a linear polyaromatic compound under conditions effective to form a reaction mixture comprising a linear polyaromatic compound-functionalized alpha olefin adduct;

b) separating the linear polyaromatic compound-functionalized alpha olefin adduct, and optionally the unreacted linear polyaromatic compound as well, from the reaction mixture, to form a functionalized adducted alpha olefin stream and a functionalized internal olefin stream;

c) dissociating the linear polyaromatic compound-functionalized alpha olefin adduct in said functionalized adducted alpha olefin stream to form a linear polyaromatic compound and a functionalized alpha olefin composition, and optionally d) separating the linear polyaromatic compound formed in step c) from a functionalized alpha olefin composition;

whereby the concentration of functionalized alpha olefin in said alpha olefin composition is enriched in functionalized alpha olefin over the concentration of functionalized alpha olefin in the feedstock.

2. The process of claim 1, wherein the feedstock is contacted with linear polyaromatic compound at a temperature ranging from 150° to about 290° C.

3. The process of claim 2, wherein the feedstock is contacted with linear polyaromatic compound at a temperature ranging from about 240° to about 265° C.

4. The process of claim 1, wherein the molar ratio of olefins in the feedstock to linear polyaromatic compound ranges from greater than 0.25:1 to 10:1.

5. The process of claim 1, wherein the linear polyaromatic compound-functionalized alpha olefin adduct is dissociated by heating the linear polyaromatic compound-functionalized alpha olefin adduct to a temperature ranging from about 250° C. to 400° C.

6. The process of claim 5, wherein the linear polyaromatic compound-functionalized alpha olefin adduct is heated to a temperature ranging from about 300° C. to 350° C.

7. The process of claim 1, wherein the separations are carried out by vacuum and/or flash distillation.

8. The process of claim 1, wherein the separations in step b) is carried out by first cooling followed by filtration or centrifugation.

9. The process of claim 1, wherein the feedstock comprises a stream derived from a Fisher-Tropsch process.

10. The process of claim 9, wherein the feedstock comprises at least 3 wt. % of functionalized alpha olefins, based on the weight of all ingredients in the feedstock.

11. The process of claim 1, wherein steps a)–c) are repeated more than once.

12. The process of claim 1, wherein the concentration of functionalized internal olefins in the functionalized alpha olefin composition is reduced by 30% or more based on the concentration of functionalized internal olefins present in the feedstock.

13. The process of claim 12, wherein the concentration of functionalized internal olefins in the functionalized alpha olefin composition is reduced by 40% or more based on the concentration of functionalized internal olefins present in the feedstock.

14. The process of claim 1, wherein the steps a)–c) are repeated more than once, and the concentration of the functionalized internal olefins in the functionalized alpha olefin composition is reduced by 40% or more in one pass.

15. The process of claim 1, wherein the feedstock comprises at least 5 wt. % of functionalized olefins, based on the weight of all ingredients in the feedstock.

16. The process of claim 15, wherein the feedstock comprises from 8 wt. % to 20 wt. % of functionalized olefins, based on the weight of all ingredients in the feedstock.

17. The process of claim 15, wherein the feedstock comprises from 3 wt. % to 18 wt. % of functionalized alpha olefins.

18. The process of claim 1, wherein the amount of functionalized alpha olefins in the feedstock is at least 20 wt. %, based on the weight of all functionalized olefins in the feedstock.

19. The process of claim 18, wherein the amount of functionalized alpha olefins in the feedstock ranges from 25 wt. % to 90 wt. %, based on the weight of all functionalized olefins in the feedstock.

20. The process of claim 1, wherein the amount of functionalized internal olefins present in the feedstock ranges from 10 wt. % to 75 wt. %, based on the weight of all functionalized olefins present in the feedstock.

21. The process of claim 1, wherein the average carbon number of the feedstock olefins ranges from 6 to 16.

22. The process of claim 1, wherein the concentration of functionalized alpha olefin in the functionalized alpha olefin composition is enriched in one pass by at least 30%, relative to the concentration of functionalized alpha olefin present in the feedstock.

23. The process of claim 1, wherein the concentration of functionalized alpha olefin in the functionalized alpha olefin composition is enriched in one pass by at least 40%, relative to the concentration of functionalized alpha olefin present in the feedstock.

24. The process of claim 1, wherein the concentration of functionalized alpha olefin in the functionalized alpha olefin composition is enriched in one pass by at least 60%, relative to the concentration of functionalized alpha olefin present in the feedstock.

25. The process of claim 1, wherein the linear polyaromatic compound formed in step c) is separated from the functionalized alpha olefin composition.

* * * * *